United States Patent
Dubois et al.

(10) Patent No.: US 9,938,225 B2
(45) Date of Patent: Apr. 10, 2018

(54) BIOMASS-DERIVED METHYL METHACRYLATE AND CORRESPONDING MANUFACTURING METHOD, USES AND POLYMERS

(71) Applicant: ARKEMA FRANCE, Colombes (FR)

(72) Inventors: Jean-Luc Dubois, Millery (FR); Jean Francois Croizy, Diesen (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 14/175,291

(22) Filed: Feb. 7, 2014

(65) Prior Publication Data

US 2014/0154758 A1     Jun. 5, 2014

Related U.S. Application Data

(62) Division of application No. 12/995,282, filed as application No. PCT/FR2009/050999 on May 28, 2009, now abandoned.

(60) Provisional application No. 61/079,823, filed on Jul. 11, 2008.

(30) Foreign Application Priority Data

May 30, 2008  (FR) ..................... 08 53588

(51) Int. Cl.

| | |
|---|---|
| *C07C 67/20* | (2006.01) |
| *C07C 69/54* | (2006.01) |
| *B32B 27/08* | (2006.01) |
| *B32B 27/20* | (2006.01) |
| *C07C 67/22* | (2006.01) |
| *B32B 27/30* | (2006.01) |
| *C08F 220/14* | (2006.01) |

(52) U.S. Cl.
CPC ............. *C07C 67/22* (2013.01); *B32B 27/08* (2013.01); *B32B 27/20* (2013.01); *B32B 27/30* (2013.01); *B32B 27/308* (2013.01); *C07C 67/20* (2013.01); *C07C 69/54* (2013.01); *C08F 220/14* (2013.01); *B32B 2250/24* (2013.01); *B32B 2419/00* (2013.01); *B32B 2432/00* (2013.01); *B32B 2605/00* (2013.01); *B32B 2605/08* (2013.01); *C07B 2200/05* (2013.01); *Y10T 428/139* (2015.01); *Y10T 428/2998* (2015.01)

(58) Field of Classification Search
CPC ................. C07C 67/20; C07C 67/22
See application file for complete search history.

(56) References Cited

U.S. PATENT DOCUMENTS

| | | | |
|---|---|---|---|
| 3,419,601 A * | 12/1968 | Isbell, Jr. ............... | C07C 67/22 423/522 |
| 6,075,162 A | 6/2000 | Kida | |
| 6,172,135 B1 | 1/2001 | Frasier et al. | |
| 6,534,592 B1 | 3/2003 | Chou et al. | |
| 7,538,247 B2 | 5/2009 | Craciun et al. | |
| 2003/0233007 A1* | 12/2003 | DeCourcy ............ | C07C 253/00 558/371 |
| 2004/0055716 A1 | 3/2004 | Landaly et al. | |
| 2005/0222458 A1 | 10/2005 | Craciun et al. | |
| 2006/0024521 A1 | 2/2006 | Everaerts et al. | |
| 2007/0123610 A1 | 5/2007 | Schultes et al. | |

OTHER PUBLICATIONS

Qureshi et al, Journal of Membrane Science, Acetone butanol ethanol (ABE) recovery by pervaporation using silicalite-silicone composite membrane from fed-batch reactor of Clostridium acetobutylicum, 2001, 187, pp. 93-102.*
Krich et al, Biomethane from Dairy Waste A Sourcebook for the Production and Use of Renewable Natural Gas in California, 2005, pp. i-G44.*
van der Drift, Synthesis Gas From Biomass for fuels and chemicals, 2006, pp. 1-31, recovered from http://www.ieatask33.org/app/webroot/files/file/ publications/syngasFromBiomassvanderDrift.pdf on Nov. 2, 2015.*
Narayan, Khemani and Scholz; Degradable Polymers and Materials, ACS Symposium Series; Chapter 18 Biobased and Biodegradable Polymer Materials: Rationale, Drivers, and Technology Exemplars, American Chemical Society: Washington, DC, 2006.*
Dubois, Selective Oxidation of Hydrocarbons and the Global Warming Problem:, Catalysis Today (2005), pp. 5-14.
Xiaobo et al., "Advances in the Research and Development of Acrylic Acid Production From Biomass", Chinese J. Chem. Eng., 14(4), pp. 419-427 (2006).
"Methacrylate De Methyle (MAM)" M Thecniques De I'Ingenieur, Traite Genie Des Procedes J 6400, pp. 1-6.

* cited by examiner

*Primary Examiner* — Paul A Zucker
(74) *Attorney, Agent, or Firm* — RatnerPrestia

(57) ABSTRACT

The invention relates to methyl methacrylate characterized in that at least one portion of the carbons thereof is biologically sourced and, more specifically, in that it contains between $0.2 \times 10^{-10}$ and $1.2 \times 10^{-10}$ wt.-% of $^{14}C$ in relation to total carbon weight according to the ASTM D6866 standard. The preparation method uses acetone cyanohydrin as a raw material, the acetone cyanohydrin being obtained by condensing cyanohydric acid on acetone, and the methyl methacrylate is prepared using a process involving the addition of methanol. According to the invention, at least one from among the acetone, cyanohydric acid and methanol is obtained by a reaction or series of reactions involving the biomass.

4 Claims, No Drawings

BIOMASS-DERIVED METHYL METHACRYLATE AND CORRESPONDING MANUFACTURING METHOD, USES AND POLYMERS

CROSS REFERENCE TO RELATED APPLICATIONS

This application is a divisional of application Ser. No. 12/995,282, filed Jul. 13, 2011, abandoned, which is the U.S. National Phase Application of PCT International Application No. PCT/FR2009/050999, filed May 28, 2009, which claims priority to U.S. Provisional Application No. 61/079,823, filed Jul. 11, 2008; the contents of such applications being incorporated herein by reference.

The present invention relates to a biomass-derived methyl methacrylate, to a method for the manufacture thereof, to the uses of this methyl methacrylate and to the polymers thereof.

Methyl methacrylate is the starting product for numerous polymerization or copolymerization reactions.

It is the monomer for the manufacture of poly(methyl methacrylate) (PMMA), known under the trademarks Altuglas® and Plexiglas®. It exists in the form of powders, granules or sheets, the powders or granules being used for molding various articles, such as articles for the car industry, household articles and office articles, and sheets finding use in signs and displays, and in the transport, building, lighting and bathroom sectors, such as antinoise walls, for works of art, flat screens, etc.

Methyl methacrylate is also the starting product for the organic synthesis of higher methacrylates, which, like methyl methacrylate, are used in the preparation of acrylic emulsions and acrylic resins, serve as additives for poly (vinyl chloride), are used as comonomers in the manufacture of numerous copolymers such as methyl methacrylate-butadiene-styrene copolymers, serve as additives for lubricants, and have many other applications among which could be mentioned medical prostheses, flocculants, cleaning products, etc. Acrylic emulsions and resins find applications in the paint, adhesive, paper, textile, ink, etc., sectors. Acrylic resins are also used in the manufacture of sheets, having the same applications as PMMA.

Methyl methacrylate can be obtained in various ways, the most common route being that with acetone cyanohydrin (Techniques de l'Ingenieur, Traite Genie des Procedes, J 6400 1-6).

In this method, acetone is reacted with hydrogen cyanide under basic catalysis in order to form acetone cyanohydrin. The latter is reacted with sulfuric acid, giving rise, through a highly exothermic reaction, to the formation of α-oxy-isobutyramide monosulfate, which is converted to sulfuric methacrylamide. The latter is then hydrolyzed and esterified with methanol to form the desired methyl methacrylate, and also ammonium hydrogen sulfate, the latter being recovered in order to regenerate the sulfuric acid.

Acetone is the coproduct of the synthesis of phenol obtained by decomposition of cumene hydroperoxide. Hydrogen cyanide is obtained either as a by-product of the synthesis of acrylonitrile by ammoxidation of propylene, or by the reaction of methane or methanol with ammonia. Ammonia was obtained by the reaction of nitrogen and hydrogen, the latter being itself generally obtained by steam reforming of methane and/or by water gas shift of the synthesis gas.

The starting materials used for the synthesis of methyl methacrylate are mainly of petroleum origin or of synthetic origin. This method thus comprises numerous sources of $CO_2$ emissions, which have been reported in the literature as being 5600 g/kg of PMMA (Catalysis Today 99, 2005, 5-14) and consequently contribute to the increase in the greenhouse effect. Given the decrease in world petroleum reserves, the source of these starting materials will gradually run out.

Biomass-derived starting materials are from a renewable source and have a smaller impact on the environment. They do not require all the refining steps, which are very expensive in terms of energy, of petroleum products. The production of $CO_2$ is reduced such that they contribute less to global warming. The plant consumed, especially for its growth, atmospheric $CO_2$ in an amount of 44 g of $CO_2$ per mole of carbon (or per 12 g of carbon). The use of a renewable source therefore begins by reducing the amount of atmospheric $CO_2$. Plant materials have the advantage that they can be cultivated in large amounts, according to demand, on most of the planet Earth, including by algae and microalgae in the marine environment.

It therefore appears to be necessary to have methods for synthesizing methyl methacrylate which are not dependent on a starting material of fossil origin, but which instead use biomass as starting material.

The term "biomass" is intended to mean starting material of plant or animal origin that is produced naturally. This plant material is characterized in that the plant has consumed atmospheric $CO_2$ for its growth, while producing oxygen. Animals, for their part, have consumed this plant starting material for their growth and have thereby assimilated the carbon derived from atmospheric $CO_2$.

The objective of the present invention is therefore to respond to certain concerns of sustainable development and to provide a methyl methacrylate in which at least a portion of the carbons thereof is of renewable origin, or biobased.

A renewable or biobased starting material is an animal or plant natural resource of which the stock can be reconstituted over a short period of time on the human scale. It is in particular necessary for this stock to be renewed as quickly as it is consumed.

Unlike materials derived from fossil materials, biobased staring materials contain $^{14}C$ in the same proportions as atmospheric $CO_2$. All the carbon samples taken from living organisms (animals or plants) are in fact a mixture of 3 isotopes: $^{12}C$ (representing approximately 98.892%), $^{13}C$ (approximately 1.108%) and $^{14}C$ (traces: $1.2 \times 10^{-10}$%). The $^{14}C/^{12}C$ ratio of living tissues is identical to that of the atmosphere. In the environment, $^{14}C$ exists in two predominant forms: in inorganic form, i.e. in the form of carbon dioxide ($CO_2$), and in organic form, i.e. in the form of carbon incorporated into organic molecules.

In a living organism, the $^{14}C/^{12}C$ ratio is kept constant by the metabolism because carbon is continually exchanged with the environment. Since the proportion of $^{14}C$ is constant in the atmosphere, the same is true in the organism, as long as it is alive, since it absorbs this $^{14}C$ in the same way that it absorbs $^{12}C$. The mean $^{14}C/^{12}C$ ratio is equal to $1.2 \times 10^{-12}$ for a biobased material, whereas a fossil starting material (for example derived from petroleum, from natural gas or from coal) has a zero ratio.

Carbon 14 is derived from the bombardment of atmospheric nitrogen (14), and is spontaneously oxidized with atmospheric oxygen to give $CO_2$. In our human history, the $^{14}CO_2$ content has increased following atmospheric nuclear explosions, and then has not stopped decreasing now that these tests have been stopped. $^{12}C$ is stable, i.e. the number of $^{12}C$ atoms in a given sample is constant over time. $^{14}C$ is, itself, radioactive (each gram of carbon of a living being contains a sufficient amount of $^{14}C$ isotopes to give 13.6 disintegrations per minute) and the number of such atoms in a sample decreases over time (t) according to the law:

$$n = no\ exp(-at),$$

in which:
no is the number of $^{14}C$ atoms at the start (on the death of the animal or plant creature),
n is the number of $^{14}C$ atoms remaining at the end of the time t,
$\underline{a}$ is the disintegration constant (or radioactive constant); it is linked to the half-life.

The half-life (or period) is the period after which any number of radioactive nuclei or of unstable particles of a given entity is reduced by half by disintegration; the half-life $T_{1/2}$ is linked to the disintegration constant $\underline{a}$ by the formula $\underline{a}\ T_{1/2} = \ln 2$. The half-life of $^{14}C$ is 5730 years. Within 50 000 years, the $^{14}C$ content is less than 0.2% of the initial content and therefore becomes difficult to detect. Petroleum products, or natural gases or coal do not therefore contain $^{14}C$.

Given the half-life ($T_{1/2}$) of $^{14}C$, the $^{14}C$ content is substantially constant from the extraction of the biobased starting materials to the manufacture of the methyl methacrylate according to the invention and even to the end of its use.

The $^{14}C$ content of a "biomaterial" can be deduced for measurements carried out, for example, according to the following techniques:
  by liquid scintillation spectrometry: this method consists in counting "Beta" particles derived from the disintegration of $^{14}C$. The Beta-radiation derived from a sample of known mass (known number of carbon atoms) is measured for a certain period of time. This "radioactivity" is proportional to the number of $^{14}C$ atoms, which can thus be determined. The $^{14}C$ present in the sample emits β-radiation which, on contact with the scintillation fluid (scintillator), gives rise to photons. These photons have different energies (between 0 and 156 Key) and form what is known as a $^{14}C$ spectrum. According to two variants of this method, the analysis relates either to the $CO_2$ previously produced by combustion of the carbon sample in an appropriate absorbent solution, or to benzene after prior conversion of the carbon sample to benzene;
  by mass spectrometry: the sample is reduced to graphite or to $CO_2$ gas, and analyzed in a mass spectrometer. This technique uses an accelerator and a mass spectrometer to separate the $^{14}C$ ions from the $^{12}C$ ions and therefore to determine the ratio of the two isotopes.

These methods of measuring the $^{14}C$ content of materials are described precisely in standards ASTM D 6866 (in particular D6866-06) and in standards ASTM D 7026 (in particular 7026-04). These methods compare the data measured on the analyzed sample with the data for a reference sample which is of 100% biobased origin, so as to give a relative percentage of biobased carbon in the sample. The $^{14}C/^{12}C$ ratio or the content by mass of $^{14}C$ relative to the total mass of carbon, can then be deduced therefrom for the sample analyzed.

The method of measurement preferably used is the mass spectrometry described in standard ASTM D6866-06 ("accelerator mass spectroscopy").

The methyl methacrylate of the present invention contains organic carbon originating from biomass, determined according to standard ASTM D6866.

The subject of the present invention is therefore firstly a methyl methacrylate characterized in that it contains from 0.2×10$^{-10}$% to 1.2×10$^{-10}$% by mass of $^{14}C$ relative to the total mass of carbon according to standard ASTM D6866, preferably from 0.4×10$^{-10}$% to 1.2×10$^{-10}$% by mass of $^{14}C$, more particularly from 0.6×10$^{-10}$% to 1.2×10$^{-10}$% by mass of $^{14}C$, even more preferably from 0.8×10$^{-10}$% to 1.2×10$^{-10}$% by mass of $^{14}C$.

In one preferred embodiment of the invention, the methyl methacrylate according to the invention contains 100% of organic carbon derived from biobased starting materials and, consequently, 1.2×10$^{-10}$% by mass of $^{14}C$ relative to the total mass of carbon.

The subject of the present invention is also a composition of monomers containing methyl methacrylate as defined above and at least one polymerizable comonomer. The polymerizable comonomer(s) is (are) in particular chosen from vinyl, vinylidene, diene and olefin monomers.

The term "vinyl monomers" is intended to mean acrylic acid or its salts of alkali or alkaline-earth metals, such as sodium, potassium or calcium, (meth)acrylates, vinylaromatic monomers, vinyl esters, (meth)acrylonitrile, (meth)acrylamide and mono- and di-(alkyl containing 1 to 22 carbon atoms)-(meth)acrylamides, and monoesters and diesters of maleic anhydride or acid.

The (meth)acrylates are in particular those of formulae, respectively:

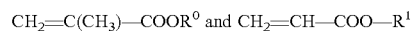

in which $R^0$ and $R^1$ are chosen from the following radicals: alkyl comprising from 1 to 22 primary, secondary or tertiary, linear or branched carbon atoms, cycloalkyl comprising from 5 to 18 carbon atoms, (alkoxy containing 1 to 18 carbon atoms)-(alkyl containing 1 to 22 carbon atoms), (alkylthio containing 1 to 18 carbon atoms)-(alkylene containing 1 to 18 carbon atoms), aryl and arylalkyl, these radicals being optionally substituted with at least one halogen atom (such as fluorine) and/or at least one hydroxyl group after protection of this hydroxyl group, the above alkyl groups being linear or branched, it being possible for $R^1$ to also represent a methyl; and glycidyl, norbornyl, naphthyl and isobornyl (meth)acrylates.

As examples of methacrylates, mention may be made of ethyl, 2,2,2-trifluoroethyl, n-propyl, isopropyl, n-butyl, sec-butyl, tert-butyl, n-amyl, i-amyl, n-hexyl, 2-ethylhexyl, cyclohexyl, octyl, i-octyl, nonyl, decyl, lauryl, stearyl, phenyl, benzyl, β-hydroxyethyl, isobornyl, hydroxypropyl and hydroxybutyl methacrylates.

As examples of acrylates of the above formula, mention may be made of methyl, ethyl, n-propyl, isopropyl, n-butyl, sec-butyl, tert-butyl, hexyl, 2-ethylhexyl, isooctyl, 3,3,5-trimethylhexyl, nonyl, isodecyl, lauryl, octadecyl, cyclohexyl, phenyl, methoxymethyl, methoxyethyl, ethoxymethyl, ethoxyethyl and perfluorooctyl acrylates.

For the purpose of the present invention, the term "vinylaromatic monomer" is intended to mean an ethylenically unsaturated aromatic monomer such as styrene, vinyltoluene, alpha-methylstyrene, 4-methylstyrene, 3-methyl styrene, 4-methoxystyrene, 2-hydroxymethylstyrene, 4-ethylstyrene, 4-ethoxystyrene, 3,4-dimethylstyrene, 2-chlorostyrene, 3-chlorostyrene, 4-chloro-3-methylstyrene, 3-tert-butylstyrene, 2,4-dichlorostyrene, 2,6-dichlorostyrene and 1-vinylnaphthalene.

As vinyl esters, mention may be made of vinyl acetate, vinyl propionate, vinyl chloride, chlorinated vinyl chloride and vinyl fluoride.

As vinylidene monomer, mention may be made of vinylidene fluoride.

The term "diene monomer" is intended to mean a diene chosen from conjugated or non-conjugated, linear or cyclic dienes such as, for example, butadiene, 2,3-dimethylbutadiene, isoprene, 1,3-pentadiene, 1,4-pentadiene, 1,4-hexadiene, 1,5-hexadiene, 1,9-decadiene, 5-methylene-2-norbornene, 5-vinyl-2-norbornene, 2-alkyl-2,5-norbornadienes, 5-ethylene-2-norbornene, 5-(2-propenyl)-2-norbornene, 5-(5-hexenyl)-2-norbornene, 1,5-cycloodadiene, bicyclo[2,2,2]octa-2,5-diene, cyclopentadiene, 4,7,8,9-tetrahydroindene and isopropylidene tetrahydroindene.

As olefin monomers, mention may be made of ethylene, butene, hexene and 1-octene. The fluorinated olefin monomers may also be mentioned.

Also forming the subject of the present invention are: a homopolymer resulting from the polymerization of methyl methacrylate as defined above, and also a copolymer obtained from a composition of monomers as defined above.

The term "copolymer" is intended to mean the copolymers obtained by polymerization of two monomers and the polymers formed from three monomers or more, such as terpolymers. The term "polymer" is intended to mean homopolymers and copolymers.

The polymers are prepared by free-radical polymerization according to techniques known to those skilled in the art. The polymerization can be carried out in the solution, in the mass, in an emulsion or in a suspension. The polymers may also be prepared by anionic polymerization.

The copolymer according to the invention may have a random, block or alternating structure.

In particular, also forming the subject of the invention is a block copolymer in which one of the blocks results from the polymerization of methyl methacrylate as defined above.

As examples of block copolymers, mention may be made of methyl methacrylate-styrene copolymers; methyl methacrylate-butadiene-styrene copolymers; styrene-butadiene-methyl methacrylate copolymers; and methyl methacrylate-butyl acrylate-methyl methacrylate copolymers.

The copolymer according to the invention may also have a core-shell structure. The term "core-shell structure" is intended to mean a multilayer structure having at least one elastomeric (or soft) layer, i.e. a layer formed from a polymer having a $T_g$ of less than −5° C., and at least one rigid (or hard) layer, i.e. formed from a polymer having a $T_g$ greater than 25° C.

Preferably, the polymer having a $T_g$ of less than −5° C. is obtained from a mixture of monomers comprising from 50 to 100 parts of at least one $C_1$-$C_{10}$ alkyl(meth)acrylate, from 0 to 50 parts of a copolymerizable monounsaturated comonomer, from 0 to 5 parts of a copolymerizable crosslinking monomer and from 0 to 5 parts of a copolymerizable grafting monomer. The $C_1$-$C_{10}$ alkyl (meth)acrylate is preferably butyl acrylate, 2-ethylhexyl acrylate or octyl acrylate.

Preferably, the polymer having a $T_g$ greater than 25° C. is obtained from a mixture of monomers comprising from 70 to 100 parts of methyl methacrylate, from 0 to 30 parts of a copolymerizable monounsaturated monomer, from 0 to 5 parts of a copolymerizable crosslinking monomer and from 0 to 5 parts of a copolymerizable grafting monomer. Preferably, the polymer having a $T_g$ greater than 25° C. has a weight-average molecular mass, expressed in PMMA equivalents, of between 10 000 and 1 000 000, advantageously between 50 000 and 500 000 g/mol.

The copolymerizable monounsaturated monomer may be a $C_1$-$C_{10}$ alkyl(meth)acrylate, styrene, alpha-methylstyrene, butylstyrene or acrylonitrile. It is preferably styrene or ethyl acrylate. The grafting monomer may be allyl(meth)acrylate, diallyl maleate or crotyl(meth)acrylate.

The crosslinking monomer may be diethylene glycol dimethacrylate, 1,3-butylene glycol dimethacrylate, 1,4-butylene glycol dimethacrylate, divinylbenzene or trimethylolpropane triacrylate (TMPTA).

In one particular embodiment of the invention, the methyl methacrylate homopolymer as defined above and/or the copolymer obtained from a composition of monomers as defined above are impact-strengthened by means of at least one impact modifier.

The impact modifier may be an acrylic elastomer such as the block copolymers methyl(meth)acrylate-styrene; butyl(meth)acrylate-styrene; styrene-butadiene-methyl(meth)acrylate; methyl(meth)acrylate-butyl acrylate-methyl(meth)acrylate, etc.

The impact modifier may also be in the form of fine multilayer particles having a core-shell structure as defined above. The multilayer particles may be of various morphologies. It is possible to use, for example, particles of the "soft-hard" type having an elastomeric nucleus (inner layer) and a rigid shelf (outer layer). European application EP 1061100 A1 describes such particles. It is also possible to use particles of the "hard-soft-hard" type having a rigid nucleus, an elastomeric intermediate layer and a rigid shell. Application US 2004/0030046 A1 describes examples of such particles. It is also possible to use particles of the "soft-hard-soft-hard" type having, in order, an elastomeric nucleus, a rigid intermediate layer, another elastomeric, intermediate layer and a rigid shell. French application FR-A-2446296 describes examples of such particles.

The present invention therefore also relates to a polymer composition containing at least one polymer as defined above, in particular a composition comprising:

a matrix polymer comprising at least one methyl methacrylate homopolymer as defined above and/or at least one copolymer as defined above; and a polymer additive, such as an impact modifier, chosen in particular from block copolymers, in particular as defined above, such as the block copolymers methyl(meth)acrylate-styrene; butyl(meth)acrylate-styrene; styrene-butadiene-methyl(meth)acrylate; methyl(meth)acrylate-butyl acrylate-methyl(meth)acrylate; etc., and polymers of the "core-shell" type, in particular as defined above.

The polymer composition may also comprise at least one additive chosen from thermal stabilizers, for example tert-dodecyl disulfide (DtDDS) or Irganox© 1076; lubricants; for example stearic acid or stearyl alcohol; flame retardants, for example antimony trioxide or a brominated or chlorinated phosphate ester; organic or inorganic pigments; anti-UV agents, for example Tinuvin© P; antioxidants, such as hindered phenolic compounds; antistatic agents; inorganic fillers, such as, for example, talc, calcium carbonate, titanium dioxide or zinc oxide, or organic fillers.

The polymer composition according to the invention may be in the form of a powder, of granules or of pellets.

The polymer composition according to the invention is in particular used for the manufacture of items and articles of everyday life. They may be, for example, boxes or casings for mowers, chainsaws, jet skis, domestic appliances, car roof boxes; car body parts; license plates; external wall panels for caravans and for mobile homes; external panels for refrigerators; panels for shower cubicles; doors of buildings; window moldings; cladding panels.

The present invention also relates to the use of a homopolymer as defined above, of a copolymer as defined above or of a polymer composition as defined above, for the manufacture of sheets, cast sheets, films, layers, fibers and tubes.

The subject of the present invention is also:
- a mutilayer structure comprising at least one layer obtained from a homopolymer, from at least one copolymer or from at least one polymer composition as defined above;
- an extrudable resin comprising a polymer matrix based on a homopolymer as defined above and/or on at least one copolymer as defined above and highly crosslinked polymer particles such as those described, for example, in patent EP 1022115;
- an acrylic emulsion or an acrylic resin, incorporating a homopolymer and/or at least one copolymer as defined above;
- a manufactured article obtained from at least one composition as defined above, such as articles for the car industry, household articles and office articles, signs and displays, articles in the transport, building, lighting and bathroom sectors;
- an article obtained by extrusion, coextrusion, hot pressing or multi-injection molding using at least one composition as defined above.

The subject of the present invention is also a method for the manufacture of a starting material containing mainly methyl methacrylate as defined above, according to which acetone cyanohydrin obtained by condensation of hydrocyanic acid with acetone is used as reactant, and methyl methacrylate is prepared by a route involving the introduction of methanol, characterized in that at least one from among acetone, hydrocyanic acid and methanol was obtained by a reaction or a succession of reactions starting from biomass.

The method according to the invention may also comprise one or more purification steps.

The expression "starting material containing mainly methyl methacrylate" means that the method results in the production of methyl methacrylate MMA possibly comprising impurities linked to the nature of the reactants used, or generated during the method, it being possible for this methyl methacrylate to then be used, optionally after a purification step, as starting material in all the applications in which it is known practice to use MMA, in particular for the uses described above, in particular for preparing monomer compositions containing MMA, an MMA homopolymer or MMA-based copolymers, or else MMA-based polymer compositions up to the obtaining of the manufactured articles described above.

A reaction scheme for manufacture of methyl methacrylate is the following:

Exploiting the Potential of Biomass as Acetone

In accordance with a first embodiment, the acetone was obtained by acetobutylic fermentation of $C_6$ and $C_5$ sugars, resulting in an acetone-butanol mixture, where appropriate with ethanol, from which the acetone was separated, for example, by distillation, in particular azeotropic distillation, or by membrane separation (for example on pervaporation membranes) or separation on silicalite (Revue de l'Institut Français du Pétrole [French Petroleum Institute Review], vol. 36, No. 3, 1981, pp. 339-347; Biotechnology Letters, vol. 4, No. 11, pp. 759-760 (1982); Advances in Applied Microbiology, volume 31, 1986, pp. 61-92; Prog. Ind. Microbiol 3(190) 73-90; Separation, Science and Technology ([28 (13 & 14), pp. 2167-2178, 1993]; Biotechnology Letters, vol. 4, No. 11, 759-760 (1982)).

The $C_6$ and $C_5$ sugars were advantageously obtained from a material with a high sugar content, chosen in particular from agricultural lignocellulosic residues and any materials of plant origin, such as cereal straw fodder, for instance wheat straw, corn straw or corn ear residues; cereal residues, for instance corn residues; cereal flours, for instance wheat flour; cereals such as wheat, barley, sorghum, corn; wood, wood waste and scraps; grains; sugarcane; sugarcane residues; pea twinings and stems; beet, molasses such as beet molasses; Jerusalem artichokes; potatoes, potato haulms, potato residues; starch; mixtures of cellulose, hemicellulose and lignin; which have been subjected, where appropriate, to a mechanical treatment, such as shredding, grinding or extrusion, and/or to a chemical treatment, such as acid or base steam treatment, and/or to an enzyme hydrolysis treatment in order to release the $C_6$ and $C_5$ sugars.

The mechanical and chemical pretreatments are intended to reduce the crystallinity of cellulose by breaking bonds and to increase the surface area of contact between cellulose and enzymes.

The hydrolysis step allows in particular the saccharification of starch in order to convert it to glucose or to convert sucrose to glucose.

In particular, an acetobutylic fermentation has been carried out with anaerobic bacteria such as *Clostridium beijerinckii*, such as VPI 5481 (ATCC 25732), 4635, 2697, 4419 (ATCC 11914), *Clostridium butylicum*, such as VPI 13436 (NRRLB-592), *Clostridium aurantibutyricum*, such as VPI 4633 (ATCC 17777), 10789 (NCIB 10659), *Clostridium acetobutylicum*, such as VPI 2673 (McClung 633), 13697 (ATCC 4259), 13698 (NRRL B—527—ATCC 824), 13693 (ATCC 8529), 2676 (McClung 635), *Clostridium toanum*, the mutants or genetically modified organisms thereof (Ap-

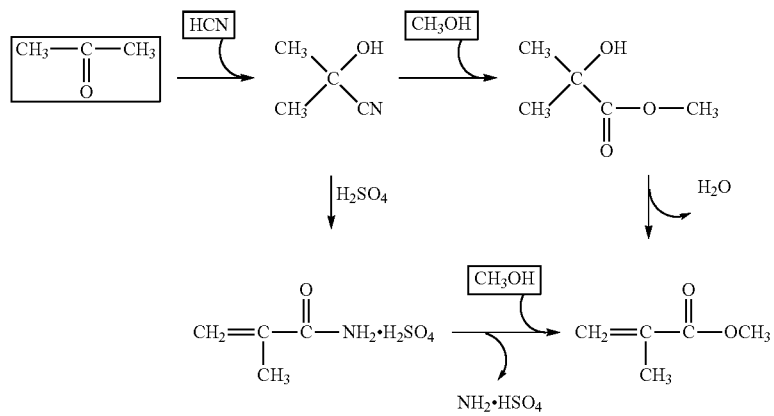

plied and Environmental Microbiology, March 1983, pp. 1160-1163, vol. 45, No. 3; Biotechnology Letters, vol. 4, No. 8 (1982) 477-482).

These fermentation methods are known to those skilled in the art who are able to choose the best working conditions for a given type of plant material (Microbiological Reviews, December 1986, vol. 50, No. 4, pp. 484-524; Bioresource Technology 42 (1992) 205-217; Appl Microbiol Biotechnol (1985) 23: 92-98; Energy from Biomass, W. Palz, Elsevier, Applied Science, London (1985), pp. 692-696).

In accordance with a second embodiment, the acetone was obtained by hydrothermal liquefaction at 573 K of sewage treatment sludge in order to obtain black water containing hydrocarbons, followed by catalytic cracking of said black water in a steam atmosphere on a catalyst based on zirconia or zirconia/alumina supported on iron oxide, and then separation of the acetone as indicated above, namely, for example, by distillation, in particular azeotropic distillation, or by membrane separation or separation on silicalite (Applied Catalysis B: Environmental 68 (2006) 154-159).

In accordance with a third embodiment, the acetone was obtained by catalytic conversion of palm oil residues on a catalyst based on zirconia or zirconia/alumina supported on iron oxide and then separation of the acetone as indicated above, namely, for example, by distillation, in particular azeotropic distillation, or by membrane separation or separation on silicalite (Applied Catalysis B: Environmental 68 (2006) 154-159).

Exploiting the Potential of Biomass as Hydrocyanic Acid and as Methanol (a) As Hydrocyanic Acid In accordance with a first embodiment, the hydrocyanic acid was obtained by ammoxidation of methane, the methane having been obtained by fermentation, in particular in the absence of oxygen, of animal and/or plant organic materials, such as pig manure, household refuse, food industry waste, resulting in a biogas mainly composed of methane and carbon dioxide, the carbon dioxide having been removed by washing the biogas with a basic aqueous solution of sodium hydroxide, potassium hydroxide or amine, or else with water under pressure, or by absorption in a solvent such as methanol.

This fermentation, also called methanization, occurs naturally or spontaneously in garbage dumps containing organic waste, but can also be carried out in digesters, in order to treat, for example, sewage treatment sludge, industrial or agricultural organic waste, pig manure and household refuse.

Preferably, the fermented mixture contains animal feces, which serve as nitrogen input necessary for the growth of the microorganisms fermenting the biomass to give methane. Reference may be made to the various methanization technologies of the prior art, to the article "Review of Current Status of Anaerobic Digestion Technology for Treatment of Municipal Solid Waste", November 1998, RISE-AT, and to the various biological methods that exist for the treatment of wastewater, for instance the Linde Laran® process.

Mention may be made of an ammoxidation of methane according to which ammonia (where appropriate obtained from biomass) is reacted with methane in the presence of air and, optionally, of oxygen on a catalyst composed of rhodium-containing platinum gauze at a temperature ranging from 1050 to 1150° C. Generally, the $CH_4/NH_3$ molar ratio ranges from 1.0 to 1.2, the $(CH_4+NH_3)$/total $O_2$ molar ratio ranges from 1.6 to 1.9; the pressure is generally from 1 to 2 bar.

In accordance with a second embodiment, the hydrocyanic acid was obtained by ammoxidation of methanol, the methanol having been obtained by pyrolysis of wood or by gasification of any materials of animal or plant origin, resulting in a syngas essentially composed of carbon monoxide and of hydrogen, which is reacted with water, or by fermentation starting from plant crops such as wheat, sugarcane or beet, giving fermentable products and therefore alcohol.

The materials of animal origin are, by way of nonlimiting examples, fish oils and fats, such as cod liver oil, whale oil, sperm whale oil, dolphin oil, seal oil, sardine oil, herring oil and shark oil, bovine, porcine, caprine, equine and poultry oils and fats, such as tallow, lard, milk fat, baking fat, chicken, cow, pig and horse fat, and the like.

The materials of plant origin are those described above as starting materials for acetobutylic fermentation. Papermill black liquor, which is a carbon-rich starting material, will be added thereto.

The method for the manufacture of HCN by ammoxidation of methanol:

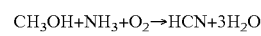

$$CH_3OH+NH_3+O_2 \rightarrow HCN+3H_2O$$

was described in particular in the 1950s-1960s in patents GB 718,112 and GB 913,836 by Distillers Company. It uses a catalyst based on molybdenum oxide at a temperature ranging from 340° C. to 450° C., or a catalyst based on antimony and tin at a temperature ranging from 350° C. to 600° C. Reference may be made to the article by Walter Sedriks in Process Economics Reviews PEP'76-3, June 1977. This method has been the subject of various improvements, in particular in terms of the catalytic systems used; mention may, for example, be made of systems based on mixed molybdenum-bismuth-iron oxides supported on silica (U.S. Pat. No. 3,911,089 by Sumitomo, U.S. Pat. No. 4,511,548 by The Standard Oil Company, JP 2002-097017 by Mitsubishi), the catalysts based on Fe—Sb—O described by Nitto Chemical Industry (EP 340 909, EP 404 529, EP 476 579, Science and Technology in Catalysis 1998, pages 335-338, Applied Catalysis A: General 194-195, 2000, 497-505) or by Mitsubishi (JP 2002-097015, JP 2002-097016, EP 832 877).

(b) As Methanol

In accordance with one particular embodiment of the present invention, the methanol was obtained as starting material in the manufacture of the methyl methacrylate of the invention, by pyrolysis of wood, by gasification or by fermentation according to what has just been described above for the production of hydrocyanic acid by ammoxidation of methanol.

According to one particular embodiment of the invention, the syngas for preparing methanol is obtained from the recovery of residual liquor from the manufacture of cellulosic pulps. Reference may be made to documents EP 666 831 and U.S. Pat. No. 7,294,225 by Chemrec, which describe in particular the gasification of residual liquors from the manufacture and bleaching of cellulose, and the production of methanol, and also to pages 92-105 of the book Procédés de pétrochimie—Caractéristiques techniques et économiques [Petrochemical Processes—technical and economical characteristics]—volume 1—Technip Editions—le gaz de synthèse et ses dérivés [syngas and derivatives thereof], which discusses the production of methanol from syngas.

The methanol used in the ammoxidation of methanol above can advantageously be biomass-derived.

Manufacture of the Starting Material Containing Mainly Methyl Methacrylate

In accordance with a first embodiment:

in a first step, hydrocyanic acid is condensed with acetone via a basic catalysis in order to obtain acetone cyanohydrin;

in a second step, the acetone cyanohydrin is reacted in a concentrated sulfuric medium in order to obtain α-oxyisobutyramide monosulfate, which is converted to sulfuric methacrylamide under the action of the heat of the reaction which is highly exothermic;

in a third step, the methacrylamide is hydrolyzed and esterified with methanol so as to form methyl methacrylate and ammonium hydrogen sulfate, and the desired starting material is recovered.

In accordance with a second embodiment:

in a first step, hydrocyanic acid is condensed with acetone via a basic catalysis in order to obtain acetone cyanohydrin;

in a second step, the acetone cyanohydrin is reacted with methanol in order to obtain methyl hydroxymethacrylate;

in a third step, the methyl hydroxymethacrylate is dehydrated so as to recover the desired starting material.

The invention also relates to the starting material containing mainly methyl methacrylate having from $0.2 \times 10^{-10}\%$ to $1.2 \times 10^{-10}\%$ by mass of $^{14}C$ relative to the total mass of carbon according to standard ASTM D6866, obtained according to the method as described above.

The following examples illustrate the present invention without, however, limiting the scope thereof. In these examples, the parts and percentages are by weight unless otherwise indicated.

EXAMPLE 1: MANUFACTURE OF ACETONE FROM WHEAT STRAW BY ENZYME HYDROLYSIS FOLLOWED BY ACETOBUTYLIC FERMENTATION

The procedure is carried out as described in the Revue de l'Institut Français de Pétrole [French Petroleum Institute Review], vol. 36, No. 3, May-June 1981, pages 339-347.

The wheat straw is shredded in a shredder and then the shredded straw is ground in a hammermill. This is followed by treatment with acid at a low concentration at a temperature of 100° C. for approximately 1 hour.

After neutralizing the acid, the medium is brought to a pH in the region of 5, which is required for enzyme hydrolysis.

A cellulose solution is prepared in the presence of nutritive elements in fermenters in series, the culturing of the microorganism *Trichoderma reesi* being carried out in the first fermenters starting from previously ground straw, and cellulose being produced in the subsequent fermenters. The desired enzyme solution is separated from the content of the final fermenter by centrifugation and filtration.

Enzyme hydrolysis of the above pretreated straw is carried out with the above enzyme solution in reactors mounted in series.

After filtration, $C_6$ and $C_5$ sugar solutions are recovered. The filtrate which contains lignin is dried so as to serve as fuel.

An acetobutylic fermentation is carried out on the above $C_6$ and $C_5$ sugar solutions using the microorganism *Clostridium acetobutylicum* under aseptic conditions.

The fermentation comprises two successive phases, the first resulting in the production of acetic acid and butylic acid, and the second resulting in the production of acetone, butanol and ethanol in the following proportions by weight: 68% butanol; 29% acetone; and 3% ethanol.

The acetone is separated by azeotropic distillation.

EXAMPLE 2: SYNTHESIS OF ACETONE CYANOHYDRIN (AC)

For this batch synthesis, a 1-liter jacketed glass reactor is used, which is equipped with mechanical stirring and surmounted by a condenser. The temperature is controlled via a circulation of cold glycol-containing water in the jacket (cryostat).

69.5 g of pure HCN and 149.4 g of acetone previously obtained by fermentation according to example 1 (equimolar mixture) are introduced into the previously cooled reactor (approximately 0° C.). As soon as the mixture reaches the temperature of 0° C., 34 mg of diethylamine (DEA) catalyst are added. The temperature passes through a maximum of 18° C. within about 6 minutes and then stabilizes rapidly at around 0° C. Samples are taken manually (approximately 1 g) over time in order to monitor the amount of unreacted HCN. The free HCN is assayed according to the Charpentier-Volhard method based on the precipitation of cyanide $CN^-$ ions, by means of an excess of N/10 silver nitrate solution and titration of the excess silver nitrate with an N/10 KSCN solution in the presence of an $Fe(SO_4)_3$ indicator in solution. After reaction for 150 minutes, a mixture comprising 1.53% by weight of free HCN, i.e. 0.533 mol/l, is obtained, which is equivalent to 10.855 mol/l of HCN converted and a degree of conversion to acetone cyanohydrin of 95.32 mol %.

The crude product is neutralized by adding excess sulfuric acid (neutralization of the basic catalyst) and then purified by vacuum distillation. The unconverted HCN and acetone are removed at the top (gradual vacuum from 760 to 30 mmHg and maximum temperature of approximately 100° C.).

EXAMPLE 3: SYNTHESIS OF ACETONE CYANOHYDRIN (AC)

The preceding example is reproduced with 69.5 g of HCN resulting from the ammoxidation of methane originating from biogas and 149.4 g of acetone previously obtained by fermentation according to example 1. The target reaction temperature is -15° C. (an exothermic peak at -9° C. is observed for 9 minutes of reaction). The free HCN is monitored as in the preceding example. After reaction for 340 minutes, a mixture is obtained which comprises 1.20% by weight of free HCN, i.e. 0.418 mol/l, which is equivalent to 10.667 mol/l of HCN converted and a degree of conversion to acetone cyanohydrin of 96.23 mol %, After distillation of the reaction product according to the preceding example, acetone cyanohydrin purified to 99.0-99.5% by weight is obtained.

EXAMPLE 4: SYNTHESIS OF SULFURIC METHYACRYLAMIDE (MACRYD)

Pure acetone cyanohydrin (AC) prepared according to the preceding examples (titer 99.06% by weight) and 100% sulfuric acid ($H_2SO_4$) containing approximately 400 ppm of phenothiazine (polymerization inhibitor) are used for the preparation of sulfuric methacrylamide.

The acetone cyanohydrin amidation reaction is carried out in a micropilot unit. The micropilot unit is composed of a stirred jacketed glass mixing reactor R1, itself composed of 3 stages each having a volume of 120 ml, and cooled with thermostated water; each stage is separated by a perforated diaphragm and stirred with a mixing turbine;

a piston flow jacketed glass precooking exchanger R1-2 having a volume of 60 ml and heated with oil;

a second stirred jacketed glass mixing reactor R2 composed of 3 stages having a volume of 120 ml, i.e. a total of 360 ml, and cooled with thermostatic water; each stage is separated by a perforated diaphragm and stirred with a mixing turbine;

a piston flow jacketed glass cooking exchanger R3 having a volume of 36 ml; and a final baffled piston flow jacketed glass cooking reactor R4 having a total volume of 240 ml and heated with oil.

This cascade of reactors operates continuously. The reactants are injected using pumps. The acetone cyanohydrin is introduced continuously into each of the stages of the reactors R1 and R2, i.e. six points of introduction. The sulfuric acid is introduced continuously at the base of the reactor R1. The reaction temperatures in R1, in R1-2, in R2, in R3 and in R4 are, respectively: 85° C., 120° C., 90° C., 140° C. and 140° C. Only the residence time in the reactor R4 is critical. The relative proportion of acetone cyanohydrin injected into R1 and R2 is 70/30, with an equal distribution in each stage of the reactors.

Two series of synthesis are carried out:
$H_2SO_4$/AC molar ratio (MR)=1.30
    total flow rate of AC: 426.33 g/h;
    flow rate of $H_2SO_4$: 632.98 g/h.
$H_2SO_4$/AC molar ratio (MR)=1.25
    total flow rate of AC: 433.54 g/h;
    flow rate of $H_2SO_4$: 618.93 g/h.

After approximately three hours of normal operation, samples are taken from each stage of reaction for analyses.

The percentages, by mass, of methacrylamide and methacrylic acid are determined by HPLC analyses after diluting the samples in a phosphate buffer medium.

The yield of (sulfuric methacrylamide+methacrylic acid) is determined at the outlet of the reactor R4 on the basis of these analyses and relative to the inflowing AC:
MR 1.30: yield 91.5 mol %;
MR 1.25: yield 90.8 mol %.

The waste (not quantified) consists mainly of carbon monoxide.

The sulfuric methacrylamide obtained is used as it is for the synthesis of methyl methacrylate.

EXAMPLE 5: SYNTHESIS OF METHYL METHACRYLATE (MMA)

The reaction for esterification of sulfuric methacrylamide with methanol is also carried out in a micropilot unit in continuous mode. Methanol originating from the reaction of a syngas obtained by gasification of black liquor is used. This second micropilot unit is composed of a 10-stage glass plate reactive column into which the sulfuric methacrylamide and a water-methanol mixture are injected countercurrentwise (reactive distillation).

At the top, the reactive column is surmounted by a distillation column filled with multiknit packing and by its condenser. It makes it possible to obtain crude methyl methacrylate.

At the base, a distiller makes it possible to collect "residual liquor", a mixture of ammonium hydrogen sulfate, sulfuric acid and water. This "residual liquor" is stripped with steam so as to recover the maximum amount of volatile organic compounds. A guard tube makes it possible to maintain a level of liquid in the distiller.

The sulfuric methacrylamide obtained in the preceding example (molar ratio 1.25, temperature approximately 130° C.) is introduced at the top of the column at a flow rate of 838.9 g/h (i.e. as AC equivalent 344 g/h). A methanol-water mixture (90-10% by weight) is introduced at two levels of the reactive column: at the base with a flow rate of 155.2 g/h, and at an intermediate point with a flow rate of 38.8 g/h (methanol/AC molar ratio: 1.35). The distiller is continuously stripped with live steam at a flow rate of 275.1 g/h (steam/AC molar ratio: 3.78 and total water/AC molar ratio: 4.05).

A methanolic solution of stabilizers containing phenothiazine is introduced at the top of the reflux column (flow rate approximately 5 g/h).

Using a timer, a crude methyl methacrylate reflux of 0.8 is maintained in the reactive column.

Once the equilibrium has been reached (approximately 3 hours), the operating conditions are the following:
distiller temperature: 125-130° C.;
reactor temperature: 110-115° C.;
reflux temperature: 87° C.

At the outlet, 3 streams are recovered: the waste at the top of the condenser, the crude MMA at the top of the distillation column, and the "residual liquor" at the outlet of the distiller. The respective flow rates are the following: 5.4 l/h, 502.4 g/h and 811.6 g/h. Their titers, expressed as % by weight, are the following:
waste: carbon monoxide 45%, dimethyl ether 40%, others 5%;
crude MMA: MMA 61.8%, methanol 11.9%, water 22.3%, other light compounds 0.5%, other heavy compounds 3.5% (i.e. an esterification yield of 92.2 mol % expressed relative to the inflowing methacrylamide);
"residual liquor": ammonium hydrogen sulfate 58.5%, $H_2SO_4$ 13.8%, $H_2O$ 23.4%, unconverted methacrylamide 0.35%, MMA 0.37%, methacrylic acid 0.43%, other compounds 3.15%.

The crude MMA is purified in the following way:
liquid-liquid extraction of the methanol with water;
topping of the light compounds by vacuum distillation;
topping of the heavy compounds by vacuum distillation.

These three operations are preferably carried out continuously and the final purity of the methyl methacrylate is greater than 99.5% by weight.

EXAMPLE 6: MASS PRODUCTION OF PMMA BY A CONTINUOUS PROCESS

A mixture containing 99.6% of methyl methacrylate of renewable origin obtained in example 5, 0.38% of n-dodecyl mercaptan and 0.02% of DTAC (1,1-di(tert-amylperoxy) cyclohexane) is continuously introduced, at −40° C., into a stirred reactor kept at 160° C. and at a pressure of 10 bar. The reactor is emptied continuously at a mass flow rate that is identical to the feed flow rate.

The heat generated by the polymerization reaction is thus consumed by the introduction of the cold mixture and the emptying of the hot reaction mixture. For a reactor volume of one liter, a feed flow rate of 2 l/h makes it possible to obtain a monomer conversion of approximately 50 mol %. The reaction liquid constantly drawn off is then degassed so as to remove the excess methyl methacrylate in a continuously fed extruder provided with degassing wells. The polymer thus obtained at the outlet of the extruder then contains 99.5% of PMMA and 0.5% of residual monomer.

EXAMPLE 7: MANUFACTURE OF PMMA BY THE CAST SHEET METHOD

A mixture containing 99.943% of methyl methacrylate obtained in example 5, 0.055% of azobisisobutyronitrile and 0.002% of terpinolene is degassed in a vacuum flask at an absolute pressure of 500 mbar at ambient temperature, kept under magnetic stirring for 20 minutes. This step makes it possible to evacuate the gases dissolved in the mixture. The mixture thus degassed is then introduced into a mold consisting of 2 glass plates of 10 mm separated by a PVC seal having a diameter of 4 mm, at ambient temperature. Pliers are used to obtain good leak-tightness of the whole. The mold is then slightly inclined and the air bubbles are driven out by squeezing the PVC seal at the highest point of the mold. The whole is then introduced into a ventilated oven. Cooking is then carried out at a temperature of 50° C. for 10 h, followed by post-cooking at 130° C. for 30 minutes. After cooking, the whole is cooled to ambient temperature. A PMMA sheet is finally obtained by dismantling the mold. The PMMA sheet contains 99% of PMMA and 1% of residual monomer.

EXAMPLE 8: MANUFACTURE OF PMMA BY THE SUSPENSION PROCESS—PREPARATION OF A SUSPENDING AGENT 120 parts of a solution of sodium hydroxide (NaOH) at 40% by weight and 630 parts of deionized water are charged to a reactor provided with stirring. 250 parts of 2-acrylamido-2-methylpropanesulfonic acid (AMPS) are slowly added to the reactor and then the pH is adjusted to between 7 and 8 with a small amount of AMPS. After sufficient sparging of the solution with nitrogen in order to remove oxygen, the reactor is heated to 50° C. and then 0.075 part of potassium persulfate and 0.025 part of sodium metabisulfite are added. The polymerization ends within 60 minutes. The solution obtained is then diluted with 4000 parts of deionized water in order to obtain a solution which has a dry residue at 160° C. of 5.5% by weight and a Brookfield viscosity of 4 Pa·s measured at 25° C.

The suspension polymerization of methyl methacrylate and ethyl acrylate is carried out in the presence of the suspending agent as obtained above.

193 parts of deionized water and 7 parts of solution previously obtained corresponding to 0.385 part of dry product are charged to a pressure-resistant stirred reactor. Oxygen is removed by sparging with nitrogen and the solution is heated to 80° C. 100 parts of a deoxygenated mixture composed of 96 parts of methyl methacrylate obtained, 4 parts of ethyl acrylate, 0.25 part of t-butylperoxy-2-ethylhexanoate and 0.25 part of butanethiol are then charged to the reactor. The reactor is then hermetically sealed, and the mixture is gradually heated to 110° C. over 120 minutes. The reactor is left at 110° C. for a further 15 minutes and is then cooled.

The polymer, in the form of beads, is separated from the aqueous solution by centrifugation, washed with deionized water and dried in an oven at 80° C.

EXAMPLE 9: MANUFACTURE OF AN IMPACT ADDITIVE FOR PMMA

The following procedure is used to prepare an impact modifier having several layers consisting of a hard core, an elastomeric soft layer and a hard crown.

The ratio of the three layers is 35/45/20 with each polymer having a refractive index of between 1.46 and 15.
The composition of the three layers is the following:
Layer 1: 74.8/25/0.2 MMA/EA/Alma
Layer 2: 83.5/15.5/1 BA/STY/Alma
Layer 3: 95/5 MMA/EA
With:
MMA: methyl methacrylate
EA: ethyl acrylate
BA: butyl acrylate
STY: styrene
Alma: allyl methacrylate.

A monomer load consisting of 14% of layer 1 emulsified in water with potassium dodecylbenzene sulfonate and potassium carbonate for controlling the pH is polymerized using potassium persulfate at 80° C. The remainder of the monomers of layer 1 (86%) are then added to the preformed emulsion and then polymerized using potassium persulfate at 80° C., while controlling the amount of surfactant added in order to avoid the formation of new particles.

Layer 2 is then added and polymerized using potassium persulfate at 80° C., while controlling the amount of surfactant added in order to avoid the formation of new particles. Layer 3 is polymerized using potassium persulfate at 80° C., also while controlling the amount of surfactant added in order to avoid the formation of new particles.

The latex obtained is then cooled and recovered by spray-drying. It can be used to increase the impact strength of PMMA by mixing, for example, in an extruder.

What is claimed:
1. A method for the manufacture methyl methacrylate, comprising:
   a) condensing hydrocyanic acid with acetone to form acetone cyanohydrin, and
   b) introducing methanol to form methyl methacrylate, wherein the acetone, hydrocyanic acid and methanol are obtained by a reaction or a succession of reactions starting from biomass, and wherein the methyl methacrylate comprises $1.2 \times 10^{-10}$% by mass of $^{14}C$ relative to the total mass of carbon according to standard ASTM D6866,
   wherein the acetone is obtained by acetobutylic fermentation of $C_6$ and $C_5$ sugars, resulting in an acetone-butanol mixture, where appropriate with ethanol, and separating the acetone by distillation or by membrane separation or by separation on silicalite, or other means of separation,
   wherein the hydrocyanic acid is obtained by ammoxidation of methane, wherein the methane is obtained by fermentation, in the absence of oxygen, of animal and/or plant organic materials, resulting in a biogas mainly composed of methane and carbon dioxide, wherein the carbon dioxide is removed by washing the biogas with a basic aqueous solution of sodium hydroxide, potassium hydroxide or amine, or else with water under pressure, or by absorption in a solvent, and
   wherein the methanol is obtained by pyrolysis of wood or by gasification of any materials of animal or plant origin, resulting in a syngas mainly composed of carbon monoxide and hydrogen which is reacted with water, or by fermentation starting from plant crops giving fermentable products and therefore alcohol.
2. The method as claimed in claim 1, wherein:
   in a first step, hydrocyanic acid is condensed with acetone via a basic catalysis in order to obtain acetone cyanohydrin;

in a second step; the acetone cyanohydrin is reacted in a concentrated sulfuric medium in order to obtain α-oxy-isobutyramide monosulfate, which is converted to sulfuric methacrylamide under the action of the heat of the reaction which is highly exothermic;

in a third step, the methacrylamide is hydrolyzed and esterified with methanol so as to form methyl methacrylate and ammonium hydrogen sulfate, and the desired starting material is recovered.

3. The method as claimed in claim 1, wherein:

in a first step, hydrocyanic acid is condensed with acetone via a basic catalysis in order to obtain acetone cyanohydrin;

in a second step, the acetone cyanohydrin is reacted with methanol in order to obtain methyl hydroxymethacrylate;

in a third step, the methyl hydroxymethacrylate is dehydrated so as to recover the desired starting material.

4. The method as claimed in claim 1, wherein the syngas for preparing the methanol is obtained from the residual liquor from the manufacture and bleaching of cellulosic pulps.

* * * * *